United States Patent [19]
Keller

[11] Patent Number: 4,826,053
[45] Date of Patent: May 2, 1989

[54] DISPENSER FOR CARTRIDGES

[76] Inventor: Wilhelm A. Keller, Riedstrasse 1, CH-6330 Cham, Switzerland

[21] Appl. No.: 70,033

[22] Filed: Jul. 6, 1987

[30] Foreign Application Priority Data

Jul. 7, 1986 [CH] Switzerland .......................... 0273186
Jan. 26, 1987 [CH] Switzerland .......................... 0025287

[51] Int. Cl.⁴ ............................................. B65D 88/54
[52] U.S. Cl. ..................................... 222/340; 222/108; 222/326
[58] Field of Search ......................... 222/145, 325–327, 222/336, 340, 389, 391, 375, 108, 109; 239/321, 322, 104

[56] References Cited

U.S. PATENT DOCUMENTS

| | | | |
|---|---|---|---|
| 2,778,541 | 1/1957 | Sherbondy | 222/391 X |
| 2,786,604 | 3/1957 | Collins | 222/391 X |
| 2,815,151 | 12/1957 | Collins | 222/391 X |
| 3,311,265 | 3/1967 | Creighton, Jr. et al. | 222/391 X |
| 3,854,629 | 12/1974 | Blieberger | 222/333 X |
| 4,009,804 | 3/1977 | Costa et al. | 222/391 |
| 4,033,484 | 7/1977 | Ornsteen | 222/391 X |
| 4,356,938 | 11/1982 | Kayser | 222/391 X |
| 4,376,498 | 3/1983 | Davis, Jr. | 222/389 X |
| 4,615,469 | 10/1986 | Kishi et al. | 222/327 |
| 4,664,299 | 5/1987 | Goncalves | 222/340 X |
| 4,681,524 | 7/1987 | Ikeda et al. | 222/391 X |

Primary Examiner—Joseph J. Rolla
Assistant Examiner—Gregory L. Huson
Attorney, Agent, or Firm—Darby & Darby

[57] ABSTRACT

When using cartridges with delivery plungers, the afterflow of the cartridge content after the action on the piston has stopped, is annoying and undesirable. In a dispenser for such cartridges, which has a ram to act upon the piston as well as a mechanism for driving the ram forward, this drawback is eliminated by the action of at least one retrieval element which is frictionally guided on a ram. The retrieval element is movable longitudinally (distance s) relative to the dispenser body and by way of retrieval springs, engaging at the retrieval element, loadable through the forward drive mechanism. In this way, immediately after each completion of the forward drive of the ram, the ram is guided back and the cartridge plunger as well as the releasable connection between cartridge and dispenser is reduced with respect to stress. This construction has application to dispensers for a single cartridge as well as for double (two-component) cartridges.

21 Claims, 2 Drawing Sheets

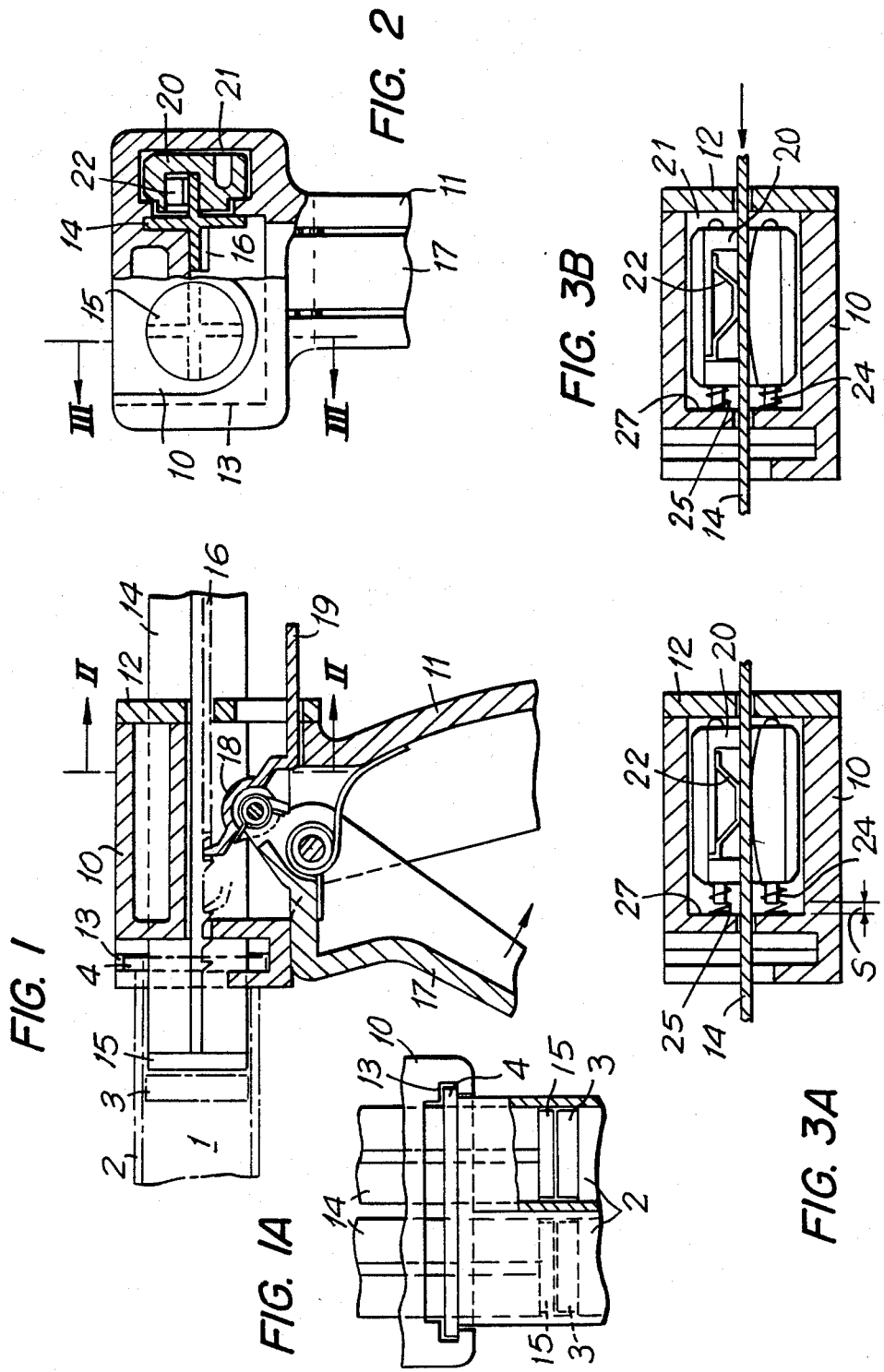

DISPENSER FOR CARTRIDGES

FIELD OF THE PRESENT INVENTION

The invention relates to a dispenser for cartridges with delivery plungers, with a ram moving longitudinally along the attachment body acting upon the delivery plunger and driving means for the ram.

BACKGROUND OF THE PRIOR ART

The exchangable cartridges intended to be used with the dispenser and to be connected with it, are generally known to be used for processing pasty or viscous substances, which are delivered through the cartridge opening by the action of the delivery plunger. A difficulty in working with cartridges of this nature consists in the fact that the contents tend to show afterflow after the action on the delivery plunger has ceased. This phenomenon is undesirable and a nuisance because it prevents clean work and makes dispensing of the exact measured amount impossible. The cause of this afterflow has been found to lie in the cartridge body's—most often manufactured as a thinwalled disposable plastic item—"breathing" upon dispensing, i.e. it elastically expands from the inside due to the pressure of the cartridge content when the plunger is advanced and assumes its original shape again when no more delivery pressure is applied. Moreover, the connection between cartridge and attachment is not completely rigid but rather is elastically deformed when the ram is advanced and subsequently recedes, which likewise contributes to afterflowing as has been observed. These phenomena are particularly pronounced and annoying when so-called double cartridges for two-component substances like glue, joint filler substances, dental impressions etc. are used with flow mixers connected to the cartridge opening since, because of the presence of the mixer, the outflow resistance and thus the internal cartridge pressure required for dispensing as well as the stress on the connection between attachment and cartridge are increased.

A primary task of the invention is to inhibit as much as possible the annoying and uncontrolled afterflow of a dispenser for cartridges after cessation of the plunger advance.

SUMMARY OF THE INVENTION

This task is solved according to the principle of the invention through design measures carried out on the dispenser, which comprises at least one retrieval element for the ram, which is connected interactively to a fixed dispenser part and also to the ram by being slidably guided on one of the mentioned parts by friction and supported at the other of these parts by at least one return spring which can be loaded by the propulsive means and is longitudinally movable by one retrieval path relative to the supporting part. This construction of the dispenser permits the ram to be brought back immediately after the propulsive force applied to it has ceased by the loaded return spring by a given amount (the so-called retrieval path), i.e. it is raised from the delivery plunger of the cartridge by which action the delivery plunger is automatically unloaded and can recede correspondingly under the internal pressure built up inside the cartridge. Simultaneously, the connection of cartridge to dispenser is freed of load so that significant causes of the afterflow are eliminated.

The invention also encompasses specific useful models of the above mentioned inventive concept such as particular specific measures for measuring the retrieve path as well as to the realization of the invention through different kinds of dispensers.

Below, embodiments of the dispenser according to the principle of the invention are explained in greater detail in conjunction with the drawing.

BRIEF DESCRIPTION OF THE DRAWING

FIG. 1 shows a longitudinal section through a dispenser according to a first embodiment with the cartridge attached to the dispenser outlined in dotted lines;

FIG. 1a is a broken-away, partial top view showing a double cartridge having two storage cylinders with plungers and held in the dispenser of FIG. 1 having a twin ram;

FIG. 2 shows the dispenser according to FIG. 1 with one half in frontal view and the other half in section along line II—II in FIG. 1;

FIGS. 3A and 3B show in section along line III—III in FIG. 2, a retrieval element in the body of the dispenser first in the starting position (3A) and then in its position during the advance of the ram (3B);

Figure 4:
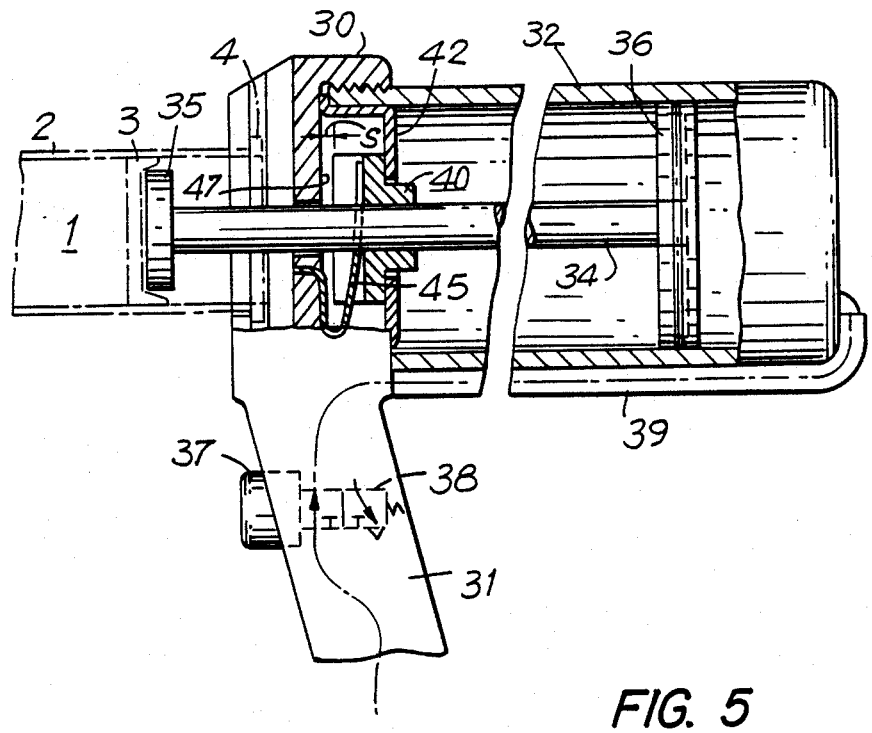
FIG. 4 represents a further model of the dispenser in longitudinal section.

The dispenser according to FIGS. 1 to 3 is intended for manual operation and is built in ways known from other "pistol-like" basic designs. The handle 11 is firmly connected to the dispenser body 10, which is shaped like a casing and is closed by a casing cover 12. These figures show a dispenser intended for use with double cartridges, the dispenser body (left side in FIG. 1) is designed so as to allow them to be held as well as exchanged. A double cartridge 1 has two parallel storage cylinders 2 adjacent to each other, which each have a delivery plunger 3 and are connected with each other at the entrance end through a flange 4, for example. When using the cartridge 1, the content to the left of the two plungers is driven out through the cartridge opening at the exit end (not shown), where customarily a flow mixer (static mixer) for mixing the two components is connected (known per se and not shown here).

The flange 4 of the cartridge 1 fastened to the dispenser engages a guide slot 13 on the front face of the dispenser body 10. For driving the delivery plunger 3 of the double cartridge, a twin ram is slidably guided longitudinally in the body 10 and the casing cover 12 consisting of two identical twin ram halves 14, each having a cross-shaped section and front disk 15; both ram halves are connected with each other at their back side (in the figure right, not visible) as is customary. For driving the twin ram forward, a longitudinal element of each ram half 14 has sawteeth 16 at its under side. A ratched tooth 18 located at the end of a hand lever 17 engages the sawteeth. The hand lever 17, in turn, is hinged to handle 11. When moving the hand lever in the direction of the arrow (FIG. 1) the twin ram is driven forward as far as needed and the delivery plungers 3 of the cartridge 1 is acted upon correspondingly. If the cartridge is to be exchanged, the ratchet tooth can be disengaged by lifting a ratchet lever and the twin ram returned to its starting position, in which the front disk 15 lies behind the slot 13 (to the right of the slot in FIG. 1).

With a lateral longitudinal element of each ram half, a retrieval element 20 is interactively connected, the structure and function of which are evident in FIGS. 2, 3A and 3B. Each retrieval element 20 is loosely guided in a side chamber 21 of the dispenser body respectively casing 10 and movable in the longitudinal direction by a distance s (FIG. 3A) relative to the stationary dispenser part 10, against which the springs 25 support themselves. Between a clamping spring 22 set into the block-shaped element 20 and an opposing face, the longitudinal element of the ram is clamped in, which creates between retrieval element and ram a frictional coupling of predetermined frictional force. Between each element 20 and the front wall 27 of the particular chamber 21 in the stationary dispenser body 10, two retrieval springs are located, which function as pressure springs 25 and are each guided on a pin 24.

When the ram 14 is not driven forward and free of load, the retrieval element 20 is in its starting position with respect to the casing 10 according to FIG. 3A. It is held in this positon as far as it will go by the springs 25 against the casing cover 12. If the ram 14 is advanced by moving the hand lever 17 and engaging the ratchet tooth 18 (arrow in FIG. 3B), the element 20 is initially taken along by way of the mentioned frictional seal until the pins 24 strike the wall 27 which loads the springs 25 (FIG. 3B); in the course of driving the rams further forward, the frictional force of the clamping springs 22 is readily overcome, with the element 20 remaining as far as it will go according to FIG. 3B. If the forward drive of the ram is stopped by releasing the hand lever 17 and the ratchet tooth 18 moves back, the springs 25 relax immediately and guide the retrieval element 20 back into the starting position according to FIG. 3A by the distance s and the ram likewise moves back by this distance through the frictional coupling and lifts itself correspondingly from the delivery plungers 3 of the cartridge. In order for the retrieval element 20 to be taken along safely to the point of contact 27, the frictional force of the friction coupling must be greater than the force of the loaded springs 25, on the other hand the springs should be somewhat pre-stressed in order to guide the nonloaded ram against the (slight) friction due to its being guided in the dispenser body (10) back to the starting position according to FIG. 3A (The above mentioned explanations refer, of course, in each instance to both of the retrieval elements 20 moved on the twin ram 14). The other embodiment of a dispenser according to FIG. 4 is intended for use with compressed air and has a cylinder/piston unit to drive the ram forward. The stationary dispenser body is formed by a top part 30 with handle 31. The top part 30 is formed for holding exchangable cartridges 1 (cartridge labeled with the same reference numbers as in FIG. 1). To the top part 30, furthermore, a compressed air cylinder 32 with piston 36 is screwed. The compressed air from an external source is supplied to the cylinder 32 preferentially via the handle 31, through a valve 38 built into the handle and actuated by a push button, and the duct 39; the valve also reduces the pressure of the cylinder 32 behind the piston 36 in a known manner when the push button 37 is not actuated. The piston rod 34 connected to the piston is guided in the top part 30 and forms the ram which acts upon the cartridge plunger 3 with the aid of a front disk 35.

On the ram 34, rests a frictionally slidable retrieval element 40. This is located between a stop face 47 of the top part 30 and a holding container 42 clamped, for example, with the cylinder 32 against the top part with a slide path s existing between the stop face 47 and the bottom of the container 42 relative to the stationary dispenser part for the retrieval element 40. Between the latter and the top part 30 is again a retrieval spring, in this case in the form of a leaf spring 45. To the friction coupling of element 40 on the ram 34 as well as to the retrieval spring 45, essentially the same reasoning applies as in the embodiment according to FIGS. 1 to 3. The frictional force of the retrieval organ 40 on the ram 34 can be set by the width of the bore or by other means, for example, by constructing the element in two parts and by bracing the two parts proportionally against the ram rod.

The operating mechanism of the dispenser according to FIG. 4 is also analogous to the previously described sample: at the beginning of the forward drive of the ram through the action of the compressed air on the piston 36, the retrieval element is in each instance taken along as far as possible until contact is made with the contact face 47 through the frictional coupling and the spring 45 correspondingly loaded, and by the pressure in cylinder 32 being reduced together with the cylinder, ventilation, which drives the ram forward, the retrieval spring 45 guides the retrieval element 40 and, through the frictional coupling, the ram 34 back by the distance s, whereby the stress on the cartridge piston and the cartridge connection at the top part 30 is reduced immediately.

Figure 5:
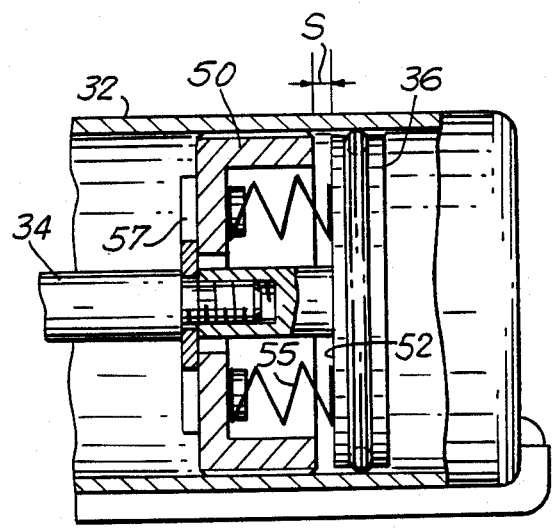
FIG. 5 shows a further model, in which in contrast to the preceding examples, the retrieval element is not guided on the ram but on the stationary cylinder of a pneumatic drive unit.

The dispenser according to FIG. 5, only partially shown here, is again intended for operation with compressed air and provided with a cylinder/piston unit to drive the ram forward. However, the arrangement of the retrieval means for the ram are "reversed" compared to the preceding embodiments, in the sense that here the retrieval element is guided along a stationary dispenser part (on the cylinder) by frictional coupling (instead of the ram), however supports itself via retrieval springs on the longitudinally movable ram (instead of a stationary part).

In the dispenser according to FIG. 5, the dispenser body with top part and handle is substantially the same as in the example according to FIG. 4 and is therefore not shown; however, the retrieval element 40, the retrieval spring 45 and the holding container 42 according to FIG. 4 become unnecessary. In their place, an annular retrieval element 50 is provided, which is slideable friction-coupling along the interior wall of the stationary cylinder 32. The ram 34 (piston rod) is screwed to the piston 36 which simultaneously holds a radial disk 57. This disk 57 and the piston side 52 facing it form bi-lateral stops for the retrieval element 50 and form a retrieval distance s by which the retrieval element is longitudinally movable relative to the ram 34. Via pressure springs 55, the element 50 supports itself on the piston 36 and thereby indirectly on the ram 34. The retrieval springs 55 in the resting state shown hold the element 50 against the stop 57 but during the drive forward of the ram 34 they are loaded, so that then the element 50 in contact is taken with the piston face 52 toward the left (in FIG. 5) and glides along the cylinder 32. When the forward drive is completed and the pressure in the cylinder to the right of the piston is removed, the retrieval element 50 remains stationary at the cylinder 32 through the frictional coupling, the springs 55 relax and guide the piston 36 with ram 34 back by the distance s in order to lift the ram from the delivery plunger in the cartridge (not visible in FIG. 5).

All described embodiments can, of course, in principle be applied to dispensers for single cartridges as well as those for double cartridges (dispensers with twin rams). The retrieval spring does not necessarily need to be a pressure spring, a tension spring placed on the opposite side of the retrieval element is also conceivable. Stops to limit the longitudinal motion of the retrieval elements are useful for defining a precise displacement path s of the ram, it is, however, also possible to limit the path during the forward drive of the ram solely through the increasing spring force of the retrieval spring with the retrieval element beginning to glide at the ram (FIGS. 1 to 4) respectively at the cylinder (FIG. 5) as soon as the spring force overcomes the adhesive friction of the friction coupling. In any case, the frictional force of the friction seal must be greater than the force of the loaded retrieval springs and this spring force in turn must be greater than the (relatively slight) friction with which the ram (and all parts connected to it) is guided along the stationary dispenser body.

While the foregoing description and drawings represent the preferred embodiments of the present invention, it will be obvious to those skilled in the art that various changes may be made therein without departing from the true spirit and scope of the present invention.

I claim:

1. In a dispenser for cartridges provided with delivery plungers, the dispenser having a ram guided longitudinally on the dispenser body for acting on the deliver plungers as well as forward drive means for the ram, the improvement comprising at least one retrieval element for the ram, which is interactively connected with a stationary dispenser part and the ram, said retrieval element being frictionally yet slidingly guided along one of the mentioned parts up to an abutting engagement against the other of these parts, and, by way of at least one retrieval spring loadable by the forward drive means, said retrieval element being movable longitudinally over a retrieval path (s) relative to the said other part, which is a supporting part for said spring, whereby, at an end of each forward thrust of said ram, as driven by said forward drive means, said ram will immediately, positively and automatically retract under the influence of said retrieval spring and frictional engagement to thereby avoid continued dispensing of any material.

2. The dispenser as in claim 1, which is formed to hold double cartridges and the ram is a twin ram.

3. The dispenser as in claim 1, wherein the length of the retrieval path (s) is limited by stops provided on said supporting part.

4. The dispenser as in claim 1 or 3, wherein, as a retrieval spring, at least one pressure spring is provided.

5. The dispenser as in claim 1 or 3, wherein the forward drive means are formed by a compressed air-driven cylinder/piston unit, the cylinder of which is connected with the dispenser body and the piston of which is connected with the ram, said retrieval element being frictionally guided at the cylinder and supported by way of springs on the piston.

6. The dispenser as in claim 1, wherein the retrieval element is frictionally guided on the ram and at the dispenser body by springs.

7. The dispenser as in claim 6, wherein the forward drive means is formed by a ratchet mechanism acting together with longitudinal sawteeth provided on the ram.

8. The dispenser as in claim 6, wherein the forward drive means are formed by a compressed air-driven cylinder/piston unit, the cylinder of which is connected with the dispenser body and the piston of which is connected to the ram (34).

9. In a dispenser for cartridges provided with delivery plungers, the dispenser having a ram guided longitudinally on the dispenser body for acting on the delivery plungers as well as forward drive means for the ram, the improvement comprising at least one retrieval element for the ram, said retrieval element being interactively connected with a stationary dispenser part and the ram and being guided, by friction coupling, along the ram; at least one retrieval spring being disposed between said stationary dispenser part and said retrieval element, said frictional coupling having an associated frictional force greater than a force stored in said retrieval spring when said spring is loaded; wherein said retrieval element, upon action of said forward drive means, being adapted to moving forward with said ram as a result of said friction coupling; forward movement of said ram over a distance (s) along a retrieval path acting to load said retrieval spring; further forward movement of said ram causing the frictional coupling between ram and retrieval element to be overcome so as to allow continued forward movement of the ram while the retrieval element is prevented from forward movement by the stationary dispenser part acting through said loaded spring; upon completion of action of said forward drive means, said loaded retrieval spring acting to cause said ram and retrieval element to immediately, positively and automatically retract to thereby avoid continued dispensing of any material from the cartridge.

10. The dispenser of claim 9 wherein said retrieval spring includes at least one pressure spring.

11. The dispenser of claim 9 wherein the forward drive means is formed by a ratchet mechanism acting together with longitudinal sawteeth provided on the ram, said ratchet mechanism allowing for reverse motion of said ram after completion of a forward drive action by said forward drive means.

12. The dispenser of claim 9 wherein the forward drive means are formed by a compressed air-driven cylinder/piston unit, the cylinder of which is connected with the dispenser body and the piston of which is connected to the ram.

13. The dispenser of claim 9, wherein said dispenser is formed to hold double cartridges and the ram is a twin ram.

14. The dispenser of claim 9 including means for limiting the length of the retrieval path (s).

15. The dispenser of claim 14 wherein said means for limiting the retrieval path length includes at least one stop.

16. In a dispenser for cartridges provided with delivery plungers, the dispenser having a ram guided longitudinally on the dispenser body for acting on the delivery plungers as well as forward drive means for the ram, the improvement comprising at least one retrieval element for the ram, said retrieval element being interactively connected with a stationary dispenser part and the ram and being guided, by frictional coupling, along said stationary dispenser part; at least one retrieval spring being disposed between said ram and retrieval element, said frictional coupling having an associated frictional force greater than a force stored in said retrieval spring when said spring is loaded; wherein, upon action of said forward drive means, said ram forwardly moves a distance (s) along a retrieval path so as to load said retrieval spring; further forward movement of said ram causing the frictional coupling between retrieval element and stationary dispenser part to be overcome so as to allow continued forward movement of said ram together with said retrieval element; upon completion of action of said forward drive means, said frictional coupling between stationary dispenser and retrieval element operating to prevent movement of said retrieval element, said loaded retrieval spring acting to cause said ram to immediately, positively and automatically retract to thereby avoid continued dispensing of any material from the cartridge.

17. The dispenser of claim 16 wherein said retrieval spring includes at least one pressure spring.

18. The dispenser of claim 16 wherein the forward drive means is formed by a ratchet mechanism acting together with longitudinal sawteeth provided on the ram, said ratchet mechanism allowing for reverse motion of said ram after completion of a forward drive action by said forward drive means.

19. The dispenser of claim 16 wherein the forward drive means are formed by a compressed air driven cylinder/piston unit, the cylinder of which is connected with the dispenser body and the piston of which is connected with the ram.

20. The dispenser of claim 16 including means for limiting the length of the retrieval path.

21. The dispenser of claim 20 wherein said means for limiting the retrieval path length includes at least one stop.

* * * * *